United States Patent [19]

Campbell

[11] 4,156,099

[45] May 22, 1979

[54] PROCESS FOR PREPARING DIHYDROXYDIPHENYL CHLOROETHYLENES

[75] Inventor: John R. Campbell, Clifton Park, N.Y.

[73] Assignee: General Electric Company, Schenectady, N.Y.

[21] Appl. No.: 896,751

[22] Filed: Apr. 17, 1978

[51] Int. Cl.$^2$ .............................................. C07C 37/00
[52] U.S. Cl. .................................................... 568/726
[58] Field of Search ........................................... 568/726

[56] References Cited

U.S. PATENT DOCUMENTS

| | | | |
|---|---|---|---|
| 4,073,814 | 2/1978 | Kinson et al. | 568/726 |
| 4,097,538 | 6/1978 | Factor et al. | 568/726 |
| 4,102,934 | 7/1978 | Quinn | 568/726 |
| 4,105,857 | 8/1978 | Campbell et al. | 568/726 |
| 4,107,442 | 8/1978 | Quinn | 568/726 |
| 4,117,018 | 9/1978 | Cleveland et al. | 568/726 |

*Primary Examiner*—Norman Morgenstern
*Attorney, Agent, or Firm*—Joseph T. Cohen; Charles T. Watts

[57] ABSTRACT

The compound 1,1-dichloro-2,2-bis-(4-hydroxyphenyl-)ethylene can be prepared by the reaction of 1,1-dichloro-2,2-diphenoxy ethylene and phenol in the presence of triflic acid. The formed dihydroxydiphenyl chloroethylene can be treated with a phosgenating agent to form polycarbonate resins which can be used in applications where flame retardancy is desired.

3 Claims, No Drawings

PROCESS FOR PREPARING DIHYDROXYDIPHENYL CHLOROETHYLENES

This invention is concerned with making dihydroxydiphenyl chloroethylenes. More particularly, the invention relates to the preparation of the compound 1,1-dichloro-2,2-bis-(4-hydroxyphenyl)ethylene having the formula

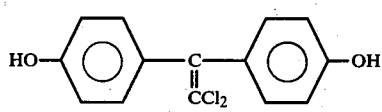

by effecting reaction between 1,1-dichloro-2,2-diphenoxy dichloroethylene of the formula

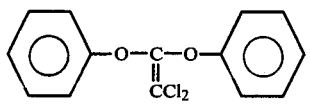

with phenol in the presence of trifluoromethanesulfonic acid also known as "triflic acid." The dihydroxydiphenyl compound of formula II can be treated with a phosgenating agent such as phosgene or diphenyl carbonate to make polycarbonate resins (as described in Polish Pat. No. 48,893 issued Dec. 12, 1964) which have good impact characteristics and flame-retardant properties. These properties recommend that such polymers be used in various molding and coating applications such as housings for electric equipment, grills for automobiles, etc.

The diphenyl dichloroethylene compound of formula II is described and can be prepared in the manner described in the copending application of Clayton B. Quinn, Ser. No. 789,020, filed April 20, 1977, and assigned to the same assignee as the present invention. By reference this application is intended to be included within the disclosures and teachings of the instant application.

The reaction between the phenol and the diphenyl dichloroethylene compound of formula II is advantageously carried out under atmospheric pressures (although superpressures are not precluded) employing at least 2 mols of the phenol per mol of the diphenyl dichloroethylene compound. Excess molar quantities of the phenol up to 15 or more mols may be used without departing from the scope of the invention.

The temperature of the reaction is not critical and can be varied widely; thus, temperatures of from about −10° to 75° C. can be advantageously employed. Usually room temperature reactions are adequate for the purpose since the reaction is exothermic and often requires cooling in order to avoid excessive heating of the reaction. The time of reaction can also be varied widely, ranging from about 1 hour to 36 hours or more, depending on the temperature at which the reaction is carried out, the proportions of ingredients, etc.

It was quite surprising to find that the trifluoromethanesulfonic acid behaved so well in converting the dichloroethylene compound of formula II to the dichloroethylene compound of formula I. First of all, it should be recognized that the use of the trifluoromethanesulfonic acid for conversion of the dichloroethylene compound of formula II permits making monomeric compounds of formula I without going through the expensive and tedious route of reacting chloral with phenol and then dehydrohalogenating the dichloroethane compound thus obtained. Also, the uniqueness of the trifluoromethanesulfonic acid was demonstrated by the fact that when quite similar acidic catalytic materials, such as trifluoroacetic acid, a mixture of trifluoroacetic acid plus boron trifluoride or a combination of trifluoroacetic acid and boron trifluoride etherate, although effective in converting the ketal of formula II to the dichloroethylene compound of formula I, the use of such acidic materials resulted in markedly lower yields of the desired compound of formula I as compared to the yields obtained using the trifluoromethanesulfonic acid. Thus, it was found that use of the trifluoromethanesulfonic acid resulted in yields ranging from about 75% to above 90% of the compound of formula I, whereas the use of the other acidic compositions gave yields ranging from about 5% to 30–35%. Additionally, these other acidic compositions introduced another complication, namely, that continued reaction in the presence of these acidic compositions seemed to cause the formation of excessive amounts of undesirable by-products, such as polymeric compositions and the less desirable ortho, para-derivative corresponding to the formula

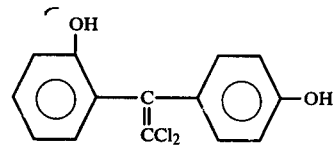

The presence of this ortho, para-isomer in the dichloroethylene compound of formula I can result in harmful effects on the properties of polycarbonate resins made from the latter dichloroethylene compound. The amount of triflic acid used is not critical and may range on a weight basis from 0.5 to 3 parts or more of the acid per part of the compound of formula II.

Inert solvents can advantageously be employed in the practice of the invention, although they are usually not necessary. Among such inert solvents may be mentioned methylene chloride, chloroform, dichloroethane, etc. The choice of the solvent medium is not critical as long as the solvent medium is liquid and is inert to the reactants and to the reaction products. Also, the solvent medium should have a boiling point sufficiently low to enable the solvent to be removed readily during isolation of the desired compound. An inert atmosphere, such as a nitrogen atmosphere, is helpful in order to minimize any side reactions.

In order that those skilled in the art may better understand how the present invention may be practiced, the following examples are given by way of illustration and not by way of limitation.

The determination of the amount of para, para-isomer obtained in the following example was carried out by silylation of the reaction mixture containing the enhanced amounts of para, para-isomer with bis(trimethylsilyl) acetamide in the manner described by Klebe et al in J.A.C.S. 88, 3390 (1966) and then analyzed by vapor phase chromatography using a 6′×⅛″ Se-30column with a temperature program of 200° to 300° C. at 10° C. per minute. VPC retention times for the ortho, para-isomer compound and the para, para-isomer compound are 6.2 and 7.4 minutes, respectively.

The diphenyl dichloroethylene compound used in the following example was prepared as follows:

To a reaction vessel were added 25 grams tetrachloroethylene, 365 ml dimethyl sulfoxide, 28.3 grams phenol and 19.83 grams potassium hydroxide. While passing nitrogen over the reaction mixture, the mixture was heated at about 135° to 140° C. for 12 hours. At the end of this time, the reaction mixture was allowed to cool, diluted with about an equal volume of water and the aqueous solution extracted three times with 200 ml diethyl ether. The combined extracts were washed three times with water, dried over magnesium sulfate, the ether evaporated, and the residue distilled to give a 50% yield of the diphenyl dichloro compound of formula II.

EXAMPLE 1

About 221.0 mg. of the diphenyl dichloroethylene compound of formula II and 0.9991 grams phenol were caused to react with stirring in the presence of 1.67 grams triflic acid at room temperature (about 25° to 27° C.) under a nitrogen atmosphere for about 2.25 hours. At the end of this time, the reaction mixture was quenched with bis(trimethylsilyl) acetamide and sufficient tetramethyl urea added to form a solution and analyzed by vpc as described above. The above reaction was repeated three times including the above-described detailed description employing different proportions of phenol to the ketal compound of formula II. The results of these three reactions are shown in the following Table I which shows the degree of conversion of the ketal of formula II to the dichloroethylene compound of formula I.

TABLE I

| Test No. | Grams Compound Formula II | Grams Phenol | Grams Triflic Acid | %[a] Yield |
|---|---|---|---|---|
| 1 | 0.5647 | 1.000 | 1.67 | 79.4 |
| 2 | 0.3312 | 1.0081 | 1.67 | 83.8 |
| 3 | 0.2210 | 0.9991 | 1.67 | 93.9[b] |

[a] Based on weight of ketal of formula II
[b] Contained less than 1 weight percent of ortho,para-isomer of formula III It will of course be apparent to those skilled in the art that in addition to the conditions under which the foregoing examples were carried out, other conditions of reaction can be employed in accordance with the above description. Moreover, within the scope of the intended invention, the amount and ratio of ingredients can also be varied widely.

What I claim as new and desire to secure by Letters Patent is:

1. The process for preparing the dihydroxydiphenyl compound, 1,1-dichloro-2,2-bis-(4-hydroxyphenyl)ethylene having the formula

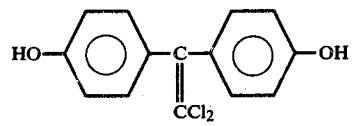

which comprises effecting reaction between 1,1-dichloro-2,2-diphenoxy ethylene with phenol in the presence of triflic acid, and thereafter isolating the aforementioned dihydroxydiphenyl compound.

2. The process as in claim 1 wherein the reaction is carried out at a temperature of from −10° to 75° C.

3. The process as in claim 1 wherein at least 2 mols phenol are employed per mol of the 1,1-dichloro-2,2-diphenoxy ethylene.

* * * * *